(12) United States Patent
Karpf et al.

(10) Patent No.: US 7,514,580 B2
(45) Date of Patent: Apr. 7, 2009

(54) PROCESS FOR THE PREPARATION OF 4,5-DIAMINO SHIKIMIC ACID DERIVATIVES

(75) Inventors: Martin Karpf, Reinach (CH); Rene Trussardi, Birsfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 494 days.

(21) Appl. No.: 11/215,753

(22) Filed: Aug. 30, 2005

(65) Prior Publication Data

US 2006/0047002 A1      Mar. 2, 2006

(30) Foreign Application Priority Data

Sep. 2, 2004      (EP)      .................. 04104227

(51) Int. Cl.
*C07C 61/22*      (2006.01)
(52) U.S. Cl. .................................. 562/507
(58) Field of Classification Search ................ 514/561; 560/125; 562/507
See application file for complete search history.

(56) References Cited

U.S. PATENT DOCUMENTS 6,462,226 B1    10/2002    Mair
2002/0095040 A1    7/2002    Karpf et al.

FOREIGN PATENT DOCUMENTS

WO    WO 98/07685    2/1998

OTHER PUBLICATIONS

J. C. Rohloff et al., J. Org. Chem. 63, 1998, 4545-4550.
Jiantao Guo and J. W. Frost, Organic Letters, vol. 6, No. 10, 2004, 1585-1588.
Protective Groups in Organic Chemistry, Theodora W. Greene et al., John Wiley & Sons Inc., New York, 1991, p. 315-385.
Advanced Organic Chemistry, ed. March J., John Wiley & Sons, New York, 1992, 353-357.
J. Org. Chem. 2001, 66, 2044-2051.
Chimia 2004, 59(9), 621.

*Primary Examiner*—Taylor Victor Oh
(74) *Attorney, Agent, or Firm*—George W. Johnston; Dennis P. Tramaloni

(57) ABSTRACT

The present invention relates to a process for the preparation of a 4,5-diamino shikimic acid derivative of formula

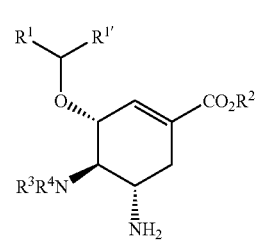

and pharmaceutically acceptable addition salts thereof wherein
$R^1$, $R^{1'}$ are independent of each other H or alkyl,
$R^2$ is an alkyl and
$R^3$, $R^4$ are independent of each other H or an alkanoyl, with the proviso that not both $R^3$ and $R^4$ are H.
4,5-diamino shikimic acid derivatives of formula I, especially the (3R,4R,5S)-5-amino-4-acetylamino-3-(1-ethyl-propoxy)-cyclohex-1-ene-carboxylic acid ethyl ester and its pharmaceutically acceptable additional salts are potent inhibitors of viral neuraminidase.

20 Claims, No Drawings

PROCESS FOR THE PREPARATION OF 4,5-DIAMINO SHIKIMIC ACID DERIVATIVES

BACKGROUND OF THE INVENTION

The present invention relates to a process for the preparation of a 4,5-diamino shikimic acid derivative of formula

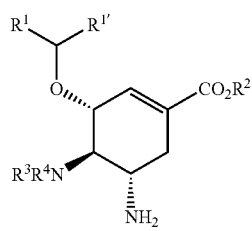

and pharmaceutically acceptable addition salts thereof
wherein
$R^1$, $R^{1'}$ are independent of each other H or alkyl,
$R^2$ is an alkyl and
$R^3$, $R^4$ are independent of each other H or an alkanoyl, with the proviso that not both $R^3$ and $R^4$ are H.

4,5-diamino shikimic acid derivatives of formula I, especially the (3R,4R,5S)-5-amino-4-acetylamino-3-(1-ethyl-propoxy)-cyclohex-1-ene-carboxylic acid ethyl ester and its pharmaceutically acceptable additional salts are potent inhibitors of viral neuramimidase (J. C. Rohloff et al., J. Org. Chem. 63, 1998, 4545-4550; WO 98/07685).

The problem at the root of the present invention is to provide a new process for preparing 4,5-diamino shikimic acid derivatives in good quality and yield from a easily obtainable starting material, 5-amino-shikimic acid. 5-amino-shikimic acid can be easily obtained from biotech processes, e.g. genetic engineering, fermentation (Jiantao Guo and J. W. Frost, Organic Letters, Vol. 6, No. 10, 2004, 1585-1588).

SUMMARY OF THE INVENTION

The problem is solved, according to the present invention, by a process for preparing the compounds of formula I as show in scheme 1:

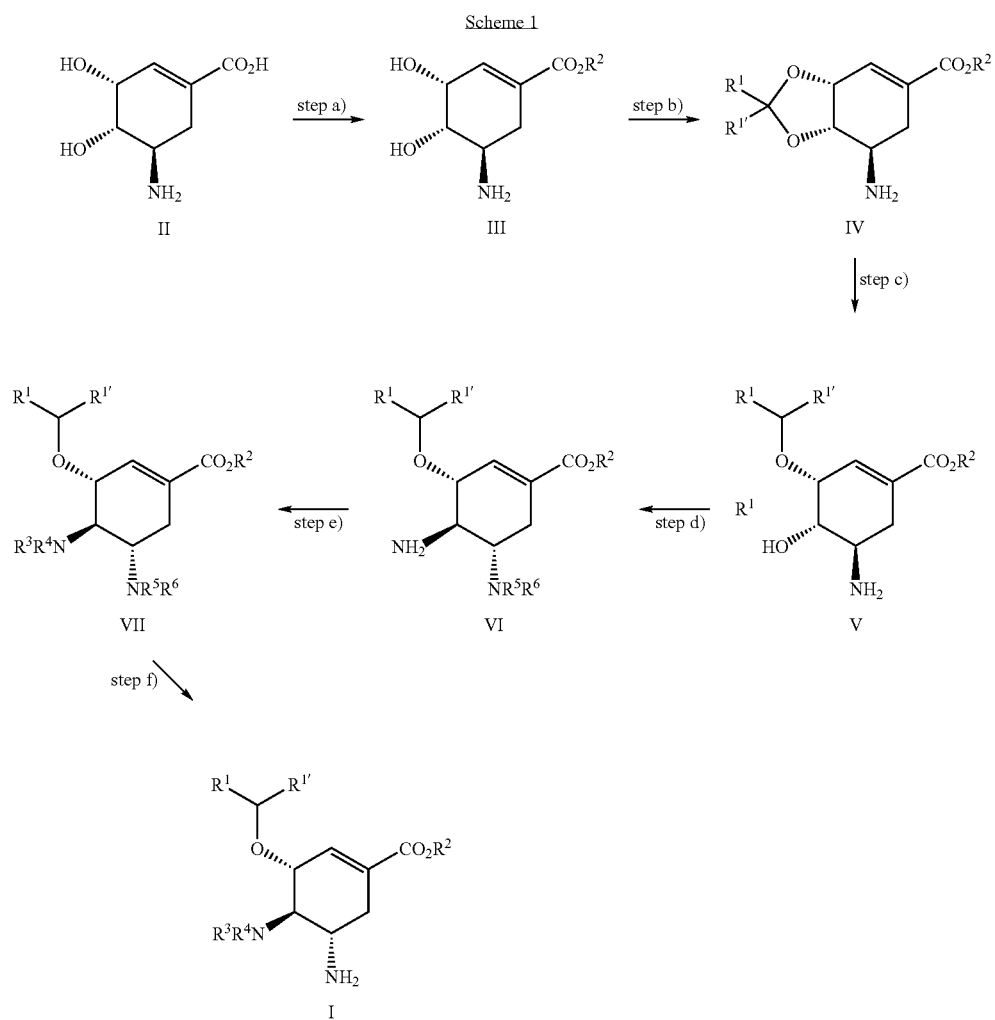

This new process has the advantage that it comprises less steps to reach 4,5-diamino shikimic acid derivatives of formula I comparing with the process known from the art (J. C. Rohloffet et al., J. Org. Chem. 63, 1998, 4545-4550; WO 98/07685).

DETAILED DESCRIPTION OF THE INVENTION

The novel process of the present invention comprises in step a):
esterifying 5-amino shikimic acid of formula

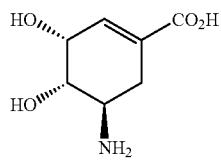

II with $R^2OH$ to form a compound of formula

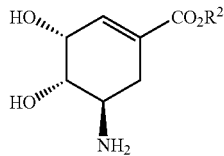

III in step b):
reacting compound of formula III with an alkanone to form a ketal of formula

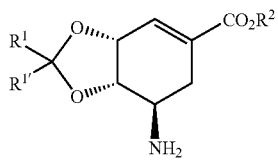

IV wherein $R^1$, $R^{1'}$ and $R^2$ are as defined above, in step c):
effecting reductive ketal opening to form a compound of formula

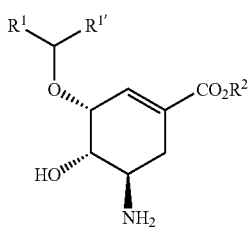

V wherein $R^1$, $R^{1'}$ and $R^2$ are as defined above, in step d):
transforming the aminoalcohol of formula V into a diamino compound of formula

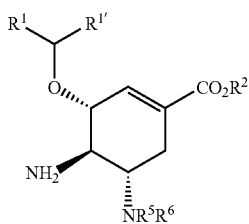

VI wherein $R^1$, $R^{1'}$ and $R^2$ are as defined above, $R^5$ and $R^6$, independently of each other, are H or an amino protecting group, with the proviso that not both $R^5$ and $R^6$ are H, in step e):
acylating the free amino function of compound of formula VI to form an acylated compound of formula

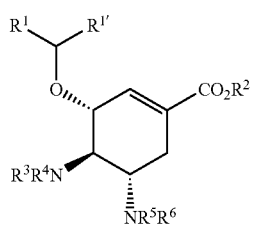

VII wherein $R^1$, $R^{1'}$, $R^2$, $R^3$, $R^4$, $R^5$ and $R^6$ are as defined above, and in step f):
reducing the compound of formula VII to compound of formula I and, if desired, forming a pharmaceutically acceptable addition salt.

The term alkyl has the meaning of a straight chained or branched alkyl group of 1 to 20 C-atoms, expediently of 1 to 12 C-atoms. Examples of such alkyl groups are methyl, ethyl, n-propyl, i-propyl, n-butyl, i-butyl, tert. butyl, pentyl and its isomers, hexyl and its isomers, heptyl and its isomers, octyl and its isomers, nonyl and its isomers, decyl and its isomers, undecyl and its isomers and dodecyl and its isomers.

This alkyl group can be substituted with one or more substituents as defined in e.g. WO 98/07685. Suitable substituents are $C_{1-6}$-alkyl (as defined above), $C_{1-6}$-alkenyl, $C_{3-6}$-cycloalkyl, hydroxy, $C_{1-6}$-alkoxy, $C_{1-6}$-alkoxycarbonyl, F, Cl, Br and I.

The term alkyl in $R^1$, $R^{1'}$ has the meaning of a straight chained or branched alkyl group of 1 to 20 C-atoms, expediently of 1 to 12 C-atoms.

Preferred meaning for $R^1$ is ethyl, for $R^{1'}$ is ethyl.

$R^2$ is a straight chained or branched alkyl group of 1 to 12 C-atoms, expediently of 1 to 6 C-atoms as exemplified above.

Preferred meaning for $R^2$ is ethyl.

$R^3$ and $R^4$ have the meaning of alkanoyl groups, more preferably $C_{1-6}$-alkanoyl such as hexanoyl, pentanoyl, butanoyl (butyryl), propanoyl (propionyl), ethanoyl (acetyl) and methanoyl (formyl).

Preferred meaning for $R^3$ is acetyl and for $R^4$ is H.

The term amino protecting group refers to any protecting group conventionally used and known in the art. They are described e.g. in "Protective Groups in Organic Chemistry", Theodora W. Greene et al., John Wiley & Sons Inc., New York, 1991, p. 315-385. Suitable amino protecting groups are also given in e.g. the WO 98/07685.

Preferred amino protecting groups for $R^5$ and $R^6$ are straight chained or branched alkenyl of 2 to 6 C-atoms, optionally substituted benzyl or tri-substituted silyl methyl or heterocyclyl methyl.

Straight chained or branched alkenyl of 2 to 6 C-atoms preferably is allyl or an analog thereof such as allyl or an allyl group which is substituted on the α-, β- or γ-carbon by one lower alkyl, lower alkenyl, lower alkynyl or aryl group. Suitable examples are e.g. 2-methylallyl, 3,3-dimethylallyl, 2-phenylallyl, or 3-methylallyl.

Preferred meaning for $R^5$ and $R^6$ are straight chained or branched alkenyl of 1 to 6 C-atoms group. Suitable examples are e.g. allyl, diallyl or 2-methylallyl.

Most preferred meaning for $R^5$ is allyl, for $R^6$ is H.

The term "pharmaceutically acceptable acid addition salts" embraces salts with inorganic and organic acids, such as hydrochloric acid, hydrobromic acid, nitric acid, sulfuric acid, phosphoric acid, citric acid, formic acid, fumaric acid, maleic acid, acetic acid, succinic acid, tartaric acid, methanesulfonic acid, p-toluenesulfonic acid, benzenesulfonic acid and the like.

The salt formation is effected with methods which are known per se and which are familiar to any person skilled in the art. Not only salts with inorganic acids, but also salts with organic acids come into consideration. Hydrochlorides, hydrobromides, sulfates, nitrates, citrates, acetates, maleates, succinates, methan-sulfonates, p-toluenesulfonates and the like are examples of such salts.

Preferred pharmaceutically acceptable acid addition salt is the 1:1 salt with phosphoric acid which can be formed preferably in ethanolic solution at a temperature of –20° C. to 60° C.

Step a)

Step a) comprises esterifying (3R,4S,5R)-5-amino-3,4-dihydroxy-cyclohex-1-enecarboxylic acid of formula II with an alcohol of formula $R^2OH$.

Typically, the reaction is performed in an alcohol, preferably ethanol in the presence of a strong acid, such as hydrogen chloride in ethanol, hydrochloric acid, hydrobromic acid, sulfuric acid, phosphoric acid, methanesulfonic acid, p-toluenesulfonic acid, benzensulfonic acid and the like, preferably hydrogen chloride in ethanol or methanesulfonic acid.

The reaction temperature mainly depends on the alcohol used, as a rule lies in the range of 60° C. to 150° C., preferably 70° C. to 100° C.

The reaction is as a rule finished after 1 to 10 hours, preferably 3 to 7 hours.

Step b)

Step b) comprises reacting compound of formula III with an alkanone.

Typically the reaction is performed in a suspension of compound of formula III, an alkanone, such as a $C_1$-$C_{12}$-alkanone, preferably 3-pentanon, and a strong acid, such as hydrochloric acid, hydrobromic acid, sulfuric acid, phosphoric acid, benzenesulfonic acid, methanesulfonic acid, p-toluenesulfonic acid and the like, preferably methanesulfonic acid.

The reaction temperature is typically in the range of 50° C. to 150° C., preferably 80° C. to 120° C.

The reaction time is as a rule 1 to 5 hours, preferably 1.5 to 2.5 hours.

Thereafter work up of the reaction mixture can happen by applying methods known to those skilled in the art. Expediently, the reaction mixture is diluted with an aprotic solvent, such as tetrahydrofuran, diisopropylether, tert.-butyl methyl ether, acetonitrile, toluene, ethyl acetate or a mixture thereof, preferably ethyl acetate and extracted with an aqueous basic solution, such as aqueous ammonium hydroxide solution, aqueous sodium carbonate solution, aqueous sodium hydrogen carbonate solution, aqueous potassium hydrogenphosphate, aqueous sodium hydrogenphosphate or aqueous amine solution, e.g. aqueous methylamine solution or aqueous ethylamine solution, preferably aqueous sodium hydrogen carbonate solution.

Step c)

The reaction of step c) is typically performed in an inert organic solvent, such as trichloromethane or dichloromethane.

A ketal opening reagent, such as borane-methyl sulfide complex/trimethylsilyltrifluoromethanesulfonate or triethylsilane/titanium tetrachloride is added to the reaction mixture at a temperature range of –70° C. to –20° C.

The reaction temperature is typically at a temperature range of –70° C. to –20° C., preferably –25° C. to –20° C.

The reaction is as a rule finished after 10 to 30 hours, preferably 24 hours.

Thereafter work up of the reaction mixture can happen by applying methods known to those skilled in the art. Expediently, the reaction mixture is washed with an aqueous basic solution, such as aqueous ammonium hydroxide solution, aqueous sodium carbonate solution, aqueous sodium hydrogen carbonate solution aqueous potassium hydrogenphosphate, aqueous sodium hydrogenphosphate or an aqueous amine solution, e.g. aqueous methylamine solution or aqueous ethylamine solution, preferably an aqueous ammonium hydroxide solution and extracted with organic solvent, such as tetrahydrofuran, diisopropylether, tert.-butyl methyl ether, acetonitrile, toluene, ethyl acetate or a mixture thereof, preferably ethyl acetate.

Step d)

step d) comprises the steps, d1) introducing an amino group substituent into the 2-aminoalcohol of formula V obtained in step c), d2) transforming the hydroxy group into a leaving group, and d3) splitting off the substituent of the amino group and transforming the reaction product using an amine of formula $R^5NHR^6$, wherein $R^5$ and $R^6$ are as above into a 1,2-diamino compound of formula VI.

Step d1)

Particularly interesting is the conversion of the amino group with a carbonyl group containing compound to form an imine, a so called "Schiff base".

Formation of a Schiff base is the preferred method for the conversion of the free amino group into the substituted amino group of the 2-aminoalcohol of formula V.

Carbonyl compounds suitable to form a Schiff base are either aldehydes or ketones. Both the aldehydes and the ketones can be aliphatic, alicyclic or aromatic, preferably aromatic.

Examples of suitable aliphatic aldehydes are propionaldehyde, 2-methylpentenal, 2-ethylbutyraldehyde, pivaldehyde, ethyl glyoxylate and chloral. An example of an alicyclic aldehyde is cyclopropan carbaldehyde. Examples of suitable aromatic aldehydes are furfural, 2-pyridinecarboxylaldehyde, 4-methoxybenzaldehyde, 3-nitrobenzaldehyde, a benzaldehyde sulfonate, a furfural sulfonate, and benzaldehyde. A particularly interesting aromatic aldehyde is benzaldehyde.

Examples of suitable aliphatic ketones are 1,1-dimethoxyacetone and 1,1-diethoxyacetone. Examples of suitable alicyclic ketones are cyclopentanone, cyclohexanone, cycloheptanone, 2-ethyl cyclohexanone and 2-methylcyclopentanone. An example of an aromatic ketone is acetophenone.

Preferred carbonyl containing compound is benzaldehyde.

The carbonyl containing compound is expediently used in an amount of 1.0 to 1.50, preferably 1.10 to 1.40 equivalents relating to the 2-aminoalcohol of formula IV.

Formation of the Schiff base is advantageously performed in a protic or aprotic solvent, preferably in an aprotic solvent.

Suitable aprotic solvents are for example tetrahydrofuran, dioxane, tert.-butyl methyl ether, diisopropylether, isopropylacetate, ethylacetate, methylacetate, acetonitrile, benzene, toluene, pyridine, methylene chloride, dimethylformamide, N-methylformamide and dimethylsulfoxide.

A preferred aprotic solvent is tert.-butyl methyl ether.

The water formed is usually removed by azeotropic distillation.

Formation of the Schiff base is advantageously carried out at temperatures between 30° C. and 180° C., preferably between 60° C. and 140° C.

Step d2)

Step d2) comprises transforming the hydroxy group into a leaving group, thereby forming an O-substituted 2-aminoalcohol.

Compounds and methods for effecting this transformation are well known in the art and described e.g. in "Advanced Organic Chemistry", ed. March J., John Wiley & Sons, New York, 1992, 353-357.

It was found that the hydroxy group is preferably transformed into a sulfonic acid ester.

Agents commonly used for producing sulfonic acid esters e.g. are the halogenides or the anhydrides of the following sulfonic acids: methane sulfonic acid, p-toluenesulfonic acid, benzensulfonic acid, p-nitrobenzenesulfonic acid, p-bromobenzenesulfonic acid or trifluoromethanesulfonic acid.

Preferred sulfonylating agent is a halogenide or the anhydride of methane sulfonic acid such as methane sulfonylchloride.

The sulfonylating agent is expediently added in an amount of 1.0 to 2.0 equivalents relating to one equivalent of the 2-aminoalcohol of formula V.

Usually the reaction in step d2) takes place in an inert solvent, preferably in the same solvent which has been used in the previous step d1) and at a reaction temperature of −20° C. to 100° C.

Step d3)

Step d3) comprises splitting off the substituent of the amino group and transforming the reaction product using an amine of formula $R^5NHR^6$, wherein $R^5$ and $R^6$ are as above into 1,2-diamino compound of formula V.

The course of the reaction in step d3) and the respective reaction conditions mainly depend on the kind of protection of the amino group in step d2).

Having a Schiff base the transformation is directly effected with the amine of formula $R^5NHR^6$, whereby having an acyl group, prior to the transformation with the amine of formula $R^5NHR^6$ a deacylation treatment has to take place first.

The term "acyl" means alkanoyl, preferably lower alkanoyl, alkoxy-carbonyl, preferably lower alkoxy-carbonyl, aryloxy-carbonyl or aroyl such as benzoyl.

In case of a Schiff base, the amine of formula $R^5NHR^6$ is used in an amount of at least two equivalents, preferably of 2.0 to 5.0, more preferably of 2.5 to 4.0 equivalents relating to one equivalent of the 2-aminoalcohol of formula V.

The solvent used in this reaction step d3) is as a rule the same as of the previous step d2). Accordingly protic or aprotic solvents, preferably aprotic solvents, such as for example tetrahydrofuran, dioxane, tert.-butyl methyl ether, diisopropylether, isopropylacetate, ethylacetate, methylacetate, acetonitrile, benzene, toluene, pyridine, methylene chloride, dimethylformamide, N-methylformamide and dimethylsulfoxide can be used. A preferred solvent is tert.-butyl methyl ether.

In case of a Schiff base the conversion is advantageously carried out at a temperature of 60° C. to 170° C., preferably of 90° C. to 130° C. and applying normal pressure to 10 bars.

In case the substituted amino group is acyl, prior to the treatment with the amine of formula $R^5NHR^6$ deacylation has to take place as mentioned above.

Deacylation can easily be effected under acidic conditions e.g. using sulfuric acid, methanesulfonic acid or p-toluenesulfonic acid in an alcohol, such as methanol, ethanol or isopropanol, preferably ethanol.

Thereby the respective sulfonate or sulfate salt of the O-substituted 2-aminoalcohol is formed.

The amine of formula $R^5NHR^6$ used in this step is allylamine, diallylamine, benzylamine, dibenzylamine or trimethylsilylamine.

The amine of the formula $R^5NHR^6$ is then suitably used in an amount of 1.0 to 5.0 equivalents, preferably of 2.0 to 4.0 equivalents relating to one equivalent of the 2-aminoalcohol of formula V.

The choice of solvents is about the same as for the conversion of the Schiff base, preferably ethyl acetate or tert.-butyl methyl ether.

The reaction temperature is chosen between 60° C. and 170° C., preferably between 90° C. and 130° C. and the pressure is selected between normal pressure and 10 bar.

When operating with a Schiff base step d) thus can efficiently be performed in a one pot synthesis without isolating the intermediates.

Step e)

Step e) comprises the acylation of the free amino function in position 1 to form an acylated 1,2-diamino compound of formula VII.

Acylation can be effected under strong acidic conditions by using acylating agents known to the skilled in the art. Acylating agent can be an aliphatic or aromatic carboxylic acid, or an activated derivative thereof, such as an acyl halide, a carboxylic acid ester or a carboxylic acid anhydride. Suitable acylating agent preferably is an acetylating agent such as acetylchloride, trifluoracteylchloride or acetic anhydride. Suitable aromatic acylating agent is benzoylchloride. Strong acids suitably used e.g. are mixtures of methane sulfonic acid and acetic acid or sulfuric acid and acetic acid.

Acylation however can also take place under non acidic conditions using e.g. N-acetyl imidazole or N-acetyl-N-methoxy acetamide.

Preferably however the acylation takes place under acidic conditions using a mixture of 0.5 to 2.0 equivalents of acetic anhydride, 0 to 15.0 equivalents of acetic acid and 0 to 2.0 equivalents of methanesulfonic acid in ethyl acetate.

An inert solvent such as tert.-butyl methyl ether may be added, it is however also possible to run the reaction without addition of any solvent.

The temperature is as a rule chosen in the range of −20° C. to 100° C.

Step f)

Step f) comprises releasing the amino group and, if necessary, further transforming the resulting 1,2-diamino compound of formula I into a pharmaceutically acceptable addition salt.

Isomerization/hydrolysis of step f) takes place in the presence of a suitable metal catalyst, expediently a precious metal catalyst such as Pt, Pd or Rh either applied on an inert support such as charcoal or alumina, or in complexed form. Preferred catalyst is 5 to 10% palladium on carbon (Pd/C).

The catalyst is suitably used in an amount of 2 to 30 wt. %, preferably, 5 to 20 wt. % relating to the 2-aminoalcohol of formula V.

The isomerization/hydrolysis is advantageously carried out in an aqueous solvent. The solvent itself can be protic or aprotic. Suitable protic solvents are e.g. alcohols such as methanol, ethanol or isopropanol. Suitable aprotic solvent is e.g. acetonitrile or dioxane.

The reaction temperature is preferably chosen in the range of 20° C. and 150° C.

It was found that isomerization/hydrolysis is preferably effected in the presence of a primary amine.

Primary amines suitably used are ethylenediamine, ethanolamine, or suitable derivatives of these primary amines mentioned hereinbefore. A particularly interesting primary amine is ethanolamine.

The primary amine is suitably used in an amount of 1.0 to 1.25 equivalents, preferably of 1.05 to 1.15 equivalents relating to the 2-aminoalcohol of formula V.

As a rule the 1,2-diamino compound of formula I can be isolated e.g. by evaporation and crystallization, but it is preferably kept in e.g. an ethanolic solution and then further transformed into a pharmaceutically acceptable addition salt following the methods described in J. C. Rohloff et al., J. Org. Chem., 1998, 63, 4545-4550; WO 98/07685).

Preferred pharmaceutically acceptable acid addition salt is the 1:1 salt with phosphoric acid which can be formed preferably in ethanolic solution at a temperature of 50° C. to −20° C.

The following examples shall illustrate the invention in more detail without limiting it.

EXAMPLE 1

Preparation of (3R,4R,5S)-5-amino-4-acetylamino-3-(1-ethyl-propoxy)-cyclohex-1-ene-carboxylic acid ethyl ester from (3R,4S,5R)-5-amino-3,4-dihydroxy-cyclohex-1-enecarboxylic acid (a). Preparation of (3R,4S,5R)-5-amino-3,4-dihydroxy-cyclohex-1-enecarboxylic acid ethyl ester
Preparation of (3R,4S,5R)-5-amino-3,4-dihydroxy-cyclohex-1-enecarboxylic acid ethyl ester methanesulfonic acid In a 500 ml round bottom flask equipped with a reflux condenser, a magnetic stirrer and an inert gas supply, 13.7 g (70.0 mmol) (3R,4S,5R)-5-amino-3,4-dihydroxy-cyclohex-1-enecarboxylic acid was suspended with 120 ml ethanol and treated with 4.50 ml (70.0 mmol) methanesulfonic acid, the mixture was heated to reflux for 1 hour, the reaction mixture was cooled to about 30° C. and evaporated in a rotary evaporator at 40° C./60 mbar. The resulting residue was treated again with 120 ml ethanol, heated to reflux for 1 hour and evaporated. This operation was repeated 6 times. The residue was dried at 50° C./10 mbar to yield as the crude intermediate 20.8 g (3R,4S,5R)-5-amino-3,4-dihydroxy-cyclohex-1-enecarboxylic acid ethyl ester methanesulfonate as a brown residue.

IR (film) 3350, 2982, 1715, 1252, 1097 cm−1; MS (electron impact) 201 M

Preparation of (3R,4S,5R)-5-amino-3,4-dihydroxy-cyclohex-1-enecarboxylic acid ethyl ester hydrochloride In a 50 ml round bottom flask equipped with a reflux condenser, a magnetic stirrer and an inert gas supply, 1.91 g (10.0 mmol) (3R,4S,5R)-5-amino-3,4-dihydroxy-cyclohex-1-enecarboxylic acid mono hydrate was suspended with 19 ml ethanol and cooled to 0-5° C., treated slowly (3 min) with 0.80 ml (11.0 mmol) thionyl chloride, then 1.28 ml (10.0 mmol) diethyl sulfite was added, the mixture was heated to reflux for 3 hours (a gas mixture was evolved), the black reaction mixture was cooled to 20-25° C., to the black suspension, 19 ml ethyl acetate was added dropwise in the course of 30 min, then the mixture was cooled to 0-5° C. and stirred for 1 hour at 0-5° C. The black suspension was filtered, the filter cake was washed portion wise with a mixture of 6.5 ml ethanol and 6.5 ml ethylacetate. The light grey crystals were dried at 40° C./10 mbar/1 h, to obtain 1.57 g (3R,4S,5R)-5-amino-3,4-dihydroxy-cyclohex-1-enecarboxylic acid ethyl ester hydrochloride, as light grey crystals.

IR (film) 3559, 2918, 1711, 1250, 1095 cm−1; MS (ion spray): 202.3 (M+H), 224.3 (M+Na) m/z mp: dec. 215° C.

(b). Preparation of (3aR,7R,7aS)-7-Amino-2,2-diethyl-3a,6,7,7a-tetrahydro-benzo [1,3]dioxole-5-carboxylic acid ethyl ester In a 25 ml two necked round bottom flask equipped with a dean stark separator, a reflux condenser, a thermometer, a magnetic stirrer and an inert gas supply, 0.90 g (4.47 mmol) (3R,4S,5R)-5-amino-3,4-dihydroxy-cyclohex-1-enecarboxylic acid ethyl ester was suspended in 9.0 ml 3-pentanon, 0.32 ml (4.92 mmol) methanesulfonic acid was added, the mixture was heated to reflux, with a dean stark separator for 2 hours. The reaction mixture was cooled to r.t., diluted with 9.0 ml ethyl acetate and the mixture was extracted with 9.0 ml 1M aqueous sodium hydrogen carbonate solution. The organic layer was dried over about 1 g sodium sulfate and filtered. The filter cake was washed with about 9 ml of ethyl acetate and the combined filtrates were evaporated in a rotary evaporator at 40° C./10 mbar to yield as the crude intermediate 1.05 g (3aR,7R,7aS)-7-amino-2,2-diethyl-3a,6,7,7a-tetrahydro-benzo[1,3]dioxole-5-carboxylic acid ethyl ester.

MS (ion spray): 270.3 M+H, 184.2 m/z (c). Preparation of (3R,4S,5R)-5-amino-3-(1-ethyl-propoxy)-4-hydroxy-cyclohex-1-enecarboxylic acid ethyl ester In a 250 ml two necked round bottom flask equipped with a thermometer, magnetic stirrer and an inert gas supply, 10.80 g (40.1 mmol) (3aR,7R,7aS)-7-amino-2,2-diethyl-3a,6,7,7a-tetrahydro-benzo[1,3]dioxole-5-carboxylic acid ethyl ester was dissolved in 110 ml dichloromethane, cooled to −70° C., 7.0 ml (44.1 mmol) triethylsilane was added at −70° C., 4.85 ml (44.1 mmol) titanium tetrachloride was added slowly to the reaction mixture at −70° C. The reaction mixture was stirred 18 h at −20° C. to −25° C., then 1.05 ml (6.6 mmol) triethylsilane was added at −20° C. to −25° C. and stirred for another 6 h at −20° C. to −25° C. The reaction mixture was added slowly to an aqueous 1M ammonium hydroxide solution. 100 ml ethyl acetate were added, the mixture was filtered and washed with 200 ml ethyl acetate. The organic layer was separated and the aqueous layer was extracted with 100 ml ethyl acetate. The combined organic layers were dried over 300 g sodium sulfate, filtered, washed with 200 ml ethyl acetate and evaporated in a rotary evaporator at 40° C./600-10 mbar to yield as the crude 12.08 g of a beige oil. Purification of the crude product was obtained via a silica column chromatography using ethyl acetate with 1% of conc. aqueous ammonia as eluent. The combined fractions were evaporated and dried on a rotary evaporator to obtain 5.1 g of (3R,4S,5R)-5-amino-3-(1-ethyl-propoxy)-4-hydroxy-cyclohex-1-enecarboxylic acid ethyl ester as a yellowish oil.

MS (ion spray): 272.3 (M+H), 294.4 (M+Na) m/z

(d). Preparation of (3R,4R,5S)-5-allylamino-4-amino-3-(1-ethyl-propoxy)-cyclohex-1-enecarboxylic acid ethyl ester In a 4 l 4-necked round bottom flask equipped with Dean-Stark trap, a thermometer, a mechanical stirrer and an inert gas supply 271.4 g of (3R,4S,5R)-5-amino-3-(1-ethyl-propoxy)-4-hydroxy-cyclohex-1-enecarboxylic acid ethyl ester obtained according to (c) were dissolved at room temperature and stirring under argon in 2710 ml of tert.-butyl methyl ether. The red solution was treated with 102.1 ml of benzaldehyde (d=1.05, 1.01 mol) and heated at reflux for 2 h during which time about 9 ml of water separated. In the course of 30 min 1350 ml of tert.-butyl methyl ether were distilled. The red solution containing the intermediate was cooled to 0° C.-5° C. and treated with 167.3 ml of triethylamine (d=0.726, 1.18 mol). Then 77.7 ml of methanesulfonyl chloride (d=1.452, 0.99 mol) were added dropwise keeping the temperature in the range of 0° C. to 5° C. in the course of 85 min during which time an orange precipitate formed. After stirring for 45 min without cooling HPLC analysis showed about 15% of the intermediate (3R, 4R, 5S)-5-(benzylidene-amino)-4-hydroxy-cyclohex-1-enecarboxylic acid ethyl ester. After dropwise addition of 7.8 ml of methanesulfonyl chloride (d=1.452, 0.09 mol) at room temperature and stirring for 10 min HPLC analysis showed about 8% of the above intermediate. After dropwise addition of 7.8 ml of methanesulfonyl chloride (d=1.452, 0.09 mol) and stirring for 15 min HPLC analysis showed less than 1% of that intermediate. The orange suspension was filtered and the yellow-orange filter cake was washed with 300 ml of tert.-butyl methyl ether. The combined filtrates (1291 g) containing the intermediate (3R,4R,5S)-5-(benzylidene-amino)-4-mesyloxy-cyclohex-1-ene carboxylic acid ethyl ester were treated with 300.5 ml of allylamine (d=0.76, 4.0 mol) and the clear red solution was heated in a 3 l autoclave under 1 bar of argon with stirring to 110° C.-111° C. in the course of 45 min, then stirred at this temperature and at a pressure of 3.5 to 4.5 bar for 15 h, cooled to less than 45° C. during 1 h. The red solution was evaporated in a rotary evaporator at 48° C./600 to 10 mbar and the remaining red gel (566 g) was dissolved with intensive stirring in a two phase mixture of 1000 ml of 2N hydrochloric acid and 1000 ml of ethyl acetate. The organic phase was extracted with 1000 ml of 2N hydrochloric acid, the combined aqueous phases were washed with 500 ml of ethyl acetate, cooled to 10° C. and treated with stirring with about 256 ml of 50% aqueous potassium hydroxide until pH=10.1 was reached keeping the temperature in the range of 10° C. to 20° C. The organic phase was separated and the aqueous phase was extracted first with 1000 ml, then with 500 ml, in total with 1500 ml of tert.-butyl methyl ether and the combined extracts were evaporated in a rotary evaporator at 48° C./340 to 10 mbar to yield crude (3R,4R,5S)-5-allylamino-4-amino-3-(1-ethyl-propoxy)-cyclohex-1-enecarboxylic acid ethyl ester (277.9 g) as a red-brown oil.

IR (film): 2966, 1715, 1463, 1244, 1090 cm$^{-1}$; MS (EI, 70 eV): 310 (M), 222, 136, 98 m/z.

(e). Preparation of (3R,4R,5S)-4-acetylamino-5-allylamino-3-(1-ethyl-propoxy)-cyclohex-1-enecarboxylic acid ethyl ester In a 4 l 4-necked round bottom flask equipped with a thermometer, a mechanical stirrer, a Claisen condenser and an inert gas supply 278.0 g of (3R,4R,5S)-5-allylamino-4-amino-3-(1-ethyl-propoxy)-cyclohex-1-enecarboxylic acid ethyl ester obtained according to (d) were dissolved at room temperature with stirring under argon in 2800 ml of tert.-butyl methyl ether. From the red solution 1400 ml of tert.-butyl methyl ether were distilled. Again 1400 ml of tert.-butyl methyl ether were added and distilled off. The red solution was cooled to 0-5° C. and treated with 512 ml of acetic acid (9.0 mol) whereby the temperature rose to about 23° C. After cooling to 0° C.-5° C. 58.1 ml of methanesulfonic acid (d=1.482, 0.90 mol) were added dropwise in the course of 27 min followed by 84.7 ml of acetic anhydride (d=1.08, 0.90 mol) added dropwise in the course of 40 min keeping the temperature in the range of 0° C. to 5° C. The brown reaction mixture was stirred without cooling for 14 h then treated with vigorous stirring with 1400 ml of water (deionized) for 30 min and the brown organic phase was extracted with 450 ml of 1M aqueous methanesulfonic acid. The combined aqueous phases (pH=1.6) were treated with stirring with about 694 ml of 50% aqueous potassium hydroxide until pH=10.0 was reached, keeping the temperature in the range of 10 to 25° C. The brown, turbid mixture was extracted first with 1000 ml then with 400 ml, in total with 1400 ml of tert.-butyl methyl ether, the combined organic extracts were stirred over 32 g of charcoal and filtered. The filter cake was washed with about 200 ml tert.-butyl methyl ether and the combined filtrates were evaporated in a rotary evaporator at 47° C./380 to 10 mbar to yield 285.4 g of brown-red, amorphous crystals which were dissolved with stirring in a mixture of 570 ml of tert.-butyl methyl ether and 285 ml of n-hexane at 50° C. The brown solution was cooled in 45 min with stirring to −20° C. to −25° C. and stirred for 5 h whereby brown crystals precipitated. The suspension was filtered over a pre-cooled (−20° C.) glass filter funnel and the filter cake was washed with a pre-cooled (−20° C.) mixture of 285 ml of tert.-butyl methyl ether and 143 ml of n-hexane and dried in a rotary evaporator at 48° C.<10 mbar to yield 200.33 g (83%) of (3R,4R,5S)-4-acetylamino-5-allylamino-3-(1-ethyl-propoxy)-cyclohex-1-enecarboxylic acid ethyl ester; m.p. 100.2° C.-104.2° C.

(f). Preparation of (3R,4R,5S)-4-acetylamino-5-amino-3-(1-ethyl-propoxy)-cyclohex-1-enecarboxylic acid ethyl ester In a 1 l 4-necked round bottom flask equipped with a thermometer, a mechanical stirrer, a reflux condenser and an inert gas supply 176.2 g of (3R,4R,5S)-4-acetylamino-5-allylamino-3-(1-ethyl-propoxy)-cyclohex-1-enecarboxylic acid ethyl ester obtained according to (d) and 30.0 ml of ethanolamine (d=1.015, 0.54 mol) were dissolved at room temperature in 880 ml of ethanol and treated with 17.6 g of 10% palladium on charcoal. The black suspension was heated to reflux for 3 h, cooled to room temperature and filtered. The filter cake was washed with 100 ml of ethanol and the combined filtrates were evaporated in a rotary evaporator at 50° C./<20 mbar. The brown, oily residue (207.3 g) was treated with 600 ml of 2N hydrochloric acid and the brown solution was distilled in a rotary evaporator at 50° C./75 mbar for 5 min. The solution was cooled to room temperature, washed with 600 ml of tert.-butyl methyl ether and treated with stirring and cooling with about 110 ml of 25% aqueous ammonia keeping the temperature below room temperature until pH=9-10 was reached and a brown emulsion formed. The emulsion was extracted three times with 600 ml, in total with 1800 ml of ethyl acetate. The combined extracts were dried over about 200 g of sodium sulfate and filtered. The filter cake was washed with about 200 ml of ethyl acetate and the combined filtrates were evaporated in a rotary evaporator at 50° C./<20 mbar to yield 158.6 g of a brown oil which was dissolved in 650 ml ethanol. The brown solution was added in the course of 1 min with stirring to a hot solution (50° C.) of 57.60 g of 85% ortho-phosphoric acid (d=1.71, 0.50 mol) in 2500 ml of ethanol. The resulting solution was cooled in the course of 1 h to 22° C. At 40° C. seed crystals of (3R,4R,5S)-4-acetylamino-5-amino-3-(1-ethyl-propoxy)-cyclohex-1-enecarboxylic acid ethyl ester (about 10 mg) were added whereby crystallization started. The beige suspension was cooled in the course of 2 h to −20° C. to −25° C. and stirred at this temperature for 5 h. The suspension was filtered over a pre-cooled (−20° C.) glass filter funnel for 2 h. The filter cake was first washed with 200 ml of ethanol pre-cooled to −25° C., then twice with 850 ml, in total with 1700 ml acetone, then twice with 1000 ml, in total with 2000 ml of n-hexane, then dried at 50° C./20 mbar for 3 h to yield 124.9 g (70%) of (3R,4R,5S)-4-acetylamino-5-amino-3-(1-ethyl-propoxy)-cyclohex-1-ene carboxylic acid ethyl ester as white crystals; m.p. 205-207° C., decomposition.

EXAMPLE 2

Preparation of (3R,4R,5S)-5-amino-4-acetylamino-3-(1-ethyl-propoxy)-cyclohex-1-ene-carboxylic acid ethyl ester from (3R,4S,5R)-5-amino-3,4-dihydroxy-cyclohex-1-enecarboxylic acid Steps (a), (b), (c), (e) and (f) were performed as described above in Example 1.

Step (d), preparation of (3R,4R,5S)-5-allylamino-4-amino-3-(1-ethyl-propoxy)-cyclohex-1-enecarboxylic acid ethyl ester from (3R,4S,5R)-5-amino-3-(1-ethyl-propoxy)-4-hydroxy-cyclohex-1-enecarboxylic acid ethyl ester, was carried out as set out below.

An autoclave with a 500 ml metal reactor equipped with a thermometer, a mechanical stirrer and an inert gas supply was charged under argon with 40.70 g of (3R,4S,5R)-5-amino-3-(1-ethyl-propoxy)-4-hydroxy-cyclohex-1-enecarboxylic acid ethyl ester (0.12 mol) obtained according to (b) and 200.0 ml of ethyl formate and the solution was heated with stirring to 100° C. at 4 to 5 bar in the course of 35 min, kept at this temperature for 6 h, then cooled to room temperature. The red solution was treated and evaporated twice with 150 ml, in total with 300 ml of toluene and evaporated at 45° C./300-15 mbar to yield as the crude intermediate 46.24 g of (3R,4R,5R)-5-formylamino-4-hydroxy-3-(1-ethyl-propoxy)-cyclohex-1-enecarboxylic acid ethyl ester as a red oil.

IR (film): 2967, 1715, 1385, 1247, 1100 cm$^{-1}$; MS (electron spray): 300 (M$^+$H$^+$), 270 (M$^-$COH), 253, 212, 138 m/z.

In a 1 l 4-necked round bottom flask equipped with a reflux condenser, a thermometer, a mechanical stirrer and an inert gas supply 46.24 g of the above crude intermediate (0.15 mol) were dissolved in 460 ml of ethyl acetate and 23.7 ml triethylamine (d=0.726, 0.17 mol). The orange solution was cooled to 0° C. to 5° C. and treated dropwise in the course of 30 min with 13.2 ml of methanesulfonyl chloride (d=1.452, 0.17 mol) during which time a white precipitate formed. After stirring for 60 min without cooling the suspension reached room temperature. After 45 min at room temperature the white suspension was filtered and the filter cake was washed with 45 ml of ethyl acetate. The combined filtrates were washed with 116 ml of 1M aqueous sodium bicarbonate solution, dried over 130 g of sodium sulfate, filtered and evaporated in a rotary evaporator at 45° C./180 to >10 mbar to yield as the crude intermediate 58.39 g of (3R,4R,5R)-5-formylamino-4-methanesulfonyloxy-3-(1-ethyl-propoxy)-cyclohex-1-enecarboxylic acid ethyl ester as an orange-red oil.

IR (film): 2967, 1715, 1358, 1177, 968 cm$^{-1}$; MS(EI, 70 eV): 377(M), 290, 244, 148, 96 m/z.

In a 1 l 4-necked round bottom flask equipped with a reflux condenser, a thermometer, a mechanical and an inert gas supply 58.39 g of the above crude intermediate were dissolved in 290 ml of ethanol. The orange solution was treated with 10.7 ml of methanesulfonic acid (d=1.482, 0.17 mol) and heated to reflux for 160 min. The red-brown reaction was evaporated in a rotary evaporator at 45° C./190 to 30 mbar and the remaining red-brown oil was treated with 260 ml of deionized water and washed with 260 ml of tert.-butyl methyl ether. The organic phase was extracted with 52 ml of deionized water and the combined aqueous phases (pH=1.3) were cooled to 0° C. to 5° C. and treated with 13.7 ml of 50% aqueous potassium hydroxide keeping the temperature below 10° C. until pH=9.4 was reached whereby a beige emulsion formed. At a pH of 6.6 260 ml of ethyl acetate was added. The aqueous phase was extracted with 70 ml of ethyl acetate and the combined organic extracts were dried over 160 g of sodium sulfate, filtered and evaporated in a rotary evaporator at 45° C./190 to 20 mbar to yield as the crude intermediate 45.66 g of (3R,4R,5R)-5-amino-4-methansulfonyloxy-3-(1-ethyl-propoxy)-cyclohex-1-ene carboxylic acid ethyl ester as a red oil.

IR (film): 1720, 1362, 1250, 1170, 1070; MS(electronspray): 350, 3(M$^+$H$^+$), 290.3, 262.1, 202.2, 184.3 m/z.

An autoclave with a 500 ml glass reactor equipped with a thermometer, a mechanical stirrer and an inert gas supply was charged under argon with a red solution of 45.66 g (0.13 mol) of the crude intermediate above and 29.5 ml of allylamine (d=0.76, 0.39 mol) and 250 ml of ethyl acetate. The mixture was heated under 1 bar of argon with stirring to 111° C. to 112° C. in the course of 45 min, kept at this temperature at about 3.5 bar for 6 h, then cooled to room temperature in the course of 50 min. The orange suspension was vigorously stirred for 20 min with 230 ml of 1M aqueous sodium bicarbonate solution. The red brown organic phase was dried over 100 g of sodium sulfate and filtered. The filter cake was washed with about 50 ml of ethyl acetate and the combined filtrates were evaporated in a rotary evaporator at 45° C./160 to 10 mbar to yield as the crude intermediate 41.80 g of (3R,4R,5S)-5-allylamino-4-amino-3-(1-ethyl-propoxy)-cyclohex-1-ene carboxylic acid ethyl ester as a red oil.

IR (film): 3441, 1707, 1462, 1262, 1063 cm$^{-1}$; MS (electronspray): 311.2(M$^+$,H$^+$), 297.2, 266.3, 245.8, 223.2 m/z.

What is claimed is:

1. A process for the preparation of a compound of the formula

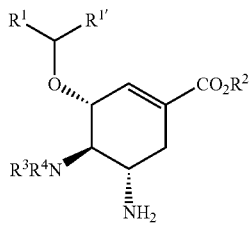

I and pharmaceutically acceptable addition salts thereof wherein
$R^1$, $R^{1'}$ are independent of each other H or $C_{1-20}$alkyl,
$R^2$ is a $C_{1-20}$alkyl and
$R^3$, $R^4$ are independent of each other H or an $C_{1-6}$alkanoyl, with the proviso that not both $R^3$ and $R^4$ are H,
which process comprises
a) esterifying 5-amino shikimic acid of formula

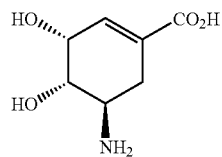

II with $R^2$OH to form a compound of formula

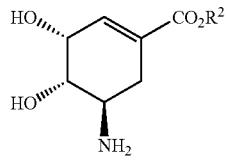

III wherein $R^2$ is as defined above;
b) reacting the compound of formula III with an alkanone to form a ketal of formula

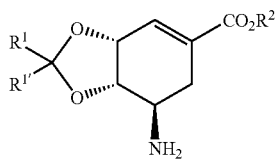

IV wherein $R^1$, $R^{1'}$ and $R^2$ are as defined above,
c) effecting reductive ketal opening to form a compound of formula

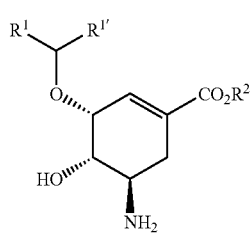

V wherein $R^1$, $R^{1'}$ and $R^2$ are as defined above, d) transforming the aminoalcohol of formula V into a diamino compound of formula

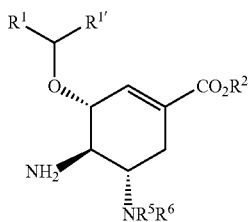

VI

By
d1) substituted or one or both hydrogens of the amino group of the compound of Formula V with an amino protecting group,
d2) esterifying the hydroxyl group to form a reactive ester leaving group, and
d3) reacting the product from steps d1) and d2) with an amine of the formula $R^5NHR^6$ to form the compound of formula VI,
wherein $R^1$, $R^{1'}$ and $R^2$ are as defined above, $R^5$ and $R^6$, independently of each other are H or an amino protecting group, with the proviso that $R^5$ and $R^6$ cannot both be H,
e) acylating the free amino function of compound of formula VI to form an acylated compound of formula

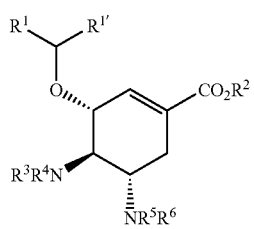

VII wherein $R^1$, $R^{1'}$, $R^2$, $R^3$, $R^4$, $R^5$ and $R^6$ are as defined above, and
f) reducing the compound of formula VII to compound of formula I and optionally further forming a pharmaceutically acceptable addition salt.

2. The process of claim 1 wherein $R^1$, $R^{1'}$ and $R^2$ are ethyl, $R^3$ is acetyl and $R^4$ is H.

3. The process of claim 1 wherein $R^5$ is allyl and $R^6$ is H.

4. The process of claim 1 wherein step a) is performed in an alcohol in the presence of a strong acid at a temperature of 60° C. to 150° C.

5. The process of claim 4 wherein the alcohol is ethanol, the strong acid is hydrochloric acid or methanesulfonic acid, and the temperature is 70° C. to 90° C.

6. The process of claim 1 wherein step b) is carried out with an alkanone in the presence of a strong acid at a temperature of 50° C. to 150° C.

7. The process of claim 6 wherein the alkanone is 3-pentanon, the strong acid is hydrochloric acid or methanesulfonic acid, and the temperature is 80° C. to 120° C.

8. The process of claim 1 wherein step c) is performed in an inert organic solvent with a ketal opening reagent at a temperature of −70° C. to −20° C.

9. The process of claim 8 wherein the inert organic solvent is dichloromethane, the ketal opening reagent is triethylsilane/titanium tetrachloride and the temperature is −25° C. to −20° C.

10. The process of claim 1 wherein the amino protecting group in step d1) is a Schiff base formed by reacting the 2-aminoalcohol of formula V with a carbonyl group containing compound or an acyl group formed by reacting the 2-aminoalcohol of formula V with an acylating agent.

11. The process of claim 10 wherein the Schiff base is formed with benzaldehyde.

12. The process of claim 1 wherein step d2) comprises the transformation of the hydroxy group into a sulfonic acid ester.

13. The process of claim 12 wherein the sulfonic acid ester is a methanesulfonic acid ester.

14. The process of claim 1 wherein the amine of formula $R^5NHR^6$ used in step d3) is allylamine, diallylamine, benzylamine, dibenzylamine or trimethylsilylamine.

15. The process of claim 14 wherein the amine of formula $R^5NHR^6$ is allylamine.

16. The process of claim 1 wherein step e) comprises the acetylation of the free amino function in position 1.

17. The process of claim 1 wherein the reaction in step f) is a isomerization/hydrolysis performed in the presence of a metal catalyst selected from the group consisting of Pt, Pd and Rh catalysts.

18. The process of claim 17 wherein the metal catalyst is a Pd/C catalyst.

19. The process of claim 17 wherein a primary amine is further added.

20. The process of claim 19 wherein the primary amine is ethanolamine.

* * * * *